(12) United States Patent
Mueller et al.

(10) Patent No.: US 6,736,001 B1
(45) Date of Patent: May 18, 2004

(54) DEVICE FOR THE NON-CONTACT STORAGE OF COMPONENTS

(75) Inventors: Gerhard Mueller, Grafing (DE); Thomas Becker, Ottobrunn (DE)

(73) Assignee: EADS Deutschland GmbH, Munich (DE)

( * ) Notice: Subject to any disclaimer, the term of this patent is extended or adjusted under 35 U.S.C. 154(b) by 0 days.

(21) Appl. No.: 09/958,957

(22) PCT Filed: Apr. 11, 2000

(86) PCT No.: PCT/DE00/01150

§ 371 (c)(1), (2), (4) Date: Jan. 16, 2002

(87) PCT Pub. No.: WO00/61467

PCT Pub. Date: Oct. 19, 2000

(30) Foreign Application Priority Data

Apr. 14, 1999 (DE) .......................................... 199 16 872

(51) Int. Cl.[7] .............................................. G01N 27/12
(52) U.S. Cl. ...................... 73/31.06; 73/23.2; 73/23.31; 73/31.01; 422/94
(58) Field of Search ............................. 73/23.2, 23.31, 73/31.01, 31.02, 31.03, 31.05, 31.06, 23.4; 422/88, 94; 338/34

(56) References Cited

U.S. PATENT DOCUMENTS

| 3,607,084 A | * | 9/1971 | Mackey et al. | ............. 73/23.31 |
| 4,633,704 A | * | 1/1987 | Tantram et al. | ............. 73/31.05 |
| 5,549,871 A | * | 8/1996 | Kocache et al. | ............... 338/34 |
| 6,453,723 B1 | * | 9/2002 | Ichikawa et al. | ............. 73/23.2 |

FOREIGN PATENT DOCUMENTS

DE 19708770 * 8/1998 ................ 73/31.06

* cited by examiner

*Primary Examiner*—Daniel S. Larkin
(74) *Attorney, Agent, or Firm*—Crowell & Moring LLP

(57) ABSTRACT

A semiconductor gas sensor, for example for measuring CO, $NO_x$, $O_3$, etc., exhibits a heatable sensor element for measuring gas concentrations, and a housing in whose interior the sensor element is disposed. The housing has a first opening, which connects the interior to the exterior. The housing has one or more second openings, which lie deeper than the first opening so that a gas stream is driven by means of convection from the second opening to the first opening. The semiconductor gas sensor can be made of silicon by means of micro engineering.

16 Claims, 2 Drawing Sheets

DEVICE FOR THE NON-CONTACT STORAGE OF COMPONENTS

BACKGROUND AND SUMMARY OF THE INVENTION

This application claims the priority of German Patent 199 16 797.4, filed Apr. 14, 1999 and PCT International No. PCT/DE00/01105 filed Apr. 11, 2000, the disclosures of which are expressly incorporated by reference herein.

The present invention relates to a semiconductor gas sensor and a process for measuring gas concentrations with a semiconductor gas sensor.

The measurement or analysis of gases is very important in different fields of technology. For example, during the combustion of fossil fuels, carbon monoxide, nitrogen oxides, and ozone are produced, which represent significant burdens on the environment and the human body. To reduce these loads, it is necessary to measure or analyze the gases generated during combustion. In particular, a measurement of the exhaust gases during the operation can reduce the emission of harmful substances by means of suitable feedback.

One possibility for gas analysis is offered by semiconductor gas sensors, where a gas sensitive layer, which changes its electric resistance when loaded with specific gases, is raised to a specific measurement temperature. By measuring the electric resistance of the sensitive layer at specific temperatures, different gas concentrations, for example of $CO$, $NO$, $NO_2$, or $O_3$, can be determined. In most cases the gas sensitive layer is a metal oxide layer, for example, of $SnO_2$.

The article by B. Ruhland et al., "Gas Kinetic Interactions of Nitrous Oxides with $SnO_2$ Surfaces", Sensors and Actuators, B50 (1998), pages 85 to 94, shows such a semiconductor gas sensor. In this prior art gas sensor, a thin layer of $SnO_2$ is disposed on a heating structure. A $SiO_2$ layer separates a heating element from the gas sensitive $SnO_2$ layer. The heating structure with the gas sensitive layer is arranged on a $Si_3N_4$ membrane, which in turn is mounted on a silicon substrate. In the measurement process, the gas sensitive layer is loaded with the gas by means of diffusion or by flow in the direction of the sensor element. The sensor element with the gas sensitive layer is arranged in a housing.

However, this presents the problem that the gas diffusion in the direction of the sensor element is prevented by means of the raising warm air or the gas, rising above the sensor element. Thus, gas streams are generated in the housing that have a negative impact on the time response of the sensor. This results in long response times and to some extent inaccurate measurement results.

Therefore, the object of the present invention is to provide a semiconductor gas sensor, which exhibits an improved time response. Furthermore, the gas sensor exhibits a compact design and is able to be produced economically. In addition, a process for measuring gas concentrations is disclosed that shows an improved time response and enables accurate measurements.

The semiconductor gas sensor of the present invention includes a heatable sensor element for measuring gas concentrations and a housing, in whose interior is disposed the sensor element. The housing exhibits a first opening, which connects the interior to the exterior, and the housing has one or more second openings, which lie deeper than the first opening in order to drive a gas stream from the second opening to the first opening by means of convection. In this manner, the response times are reduced, while the measurement accuracy is high and the cost is low.

The second openings or the gas inlet openings are arranged on the side walls preferably in the bottom part of the housing; and the first opening can be arranged on the upper side of the housing. Preferably, the second openings are arranged on the same level or deeper than the sensor element. The result is optimal gas flow in the interior of the housing.

Preferably, the housing is made of silicon by means of micro engineering. In this respect, the sensor element can be integrated into two silicon troughs, which are stacked either one above the other or opposite each other. The second openings are formed between the mutual interfaces of the troughs. In particular, the first opening is formed in the top silicon trough over the sensor element. Preferably, the second openings, which form the gas inlet openings, are formed by means of passages or channels, located between the silicon troughs. This type of construction allows an especially simple and economical production, whereby the sensor can be realized so as to be extremely compact.

Perfusible elements for filtering or reaction of the gas can be disposed in the second opening(s) or gas inlet opening(s). In this respect, the inside surface of the perfusible element exhibit for example, a material that subjects the gas flowing through to a chemical and/or catalytic reaction, before said gas reaches the sensor element. Thus, the sensitivity of the sensor can be set or changed for different gases.

Another aspect of the invention provides a process for measuring gas concentrations with a semiconductor gas sensor, wherein a gas stream is driven by means of convection through a housing. The gas flows through the housing from the bottom to the top and is guided past a sensor element, which produces a measurement signal as a function of the gas concentration.

Other objects, advantages, and novel features of the present invention will become apparent from the following detailed description of the invention when considered in conjunction with the accompanying drawings.

DETAILED DESCRIPTION OF THE PREFERRED EMBODIMENTS

Figure 1:
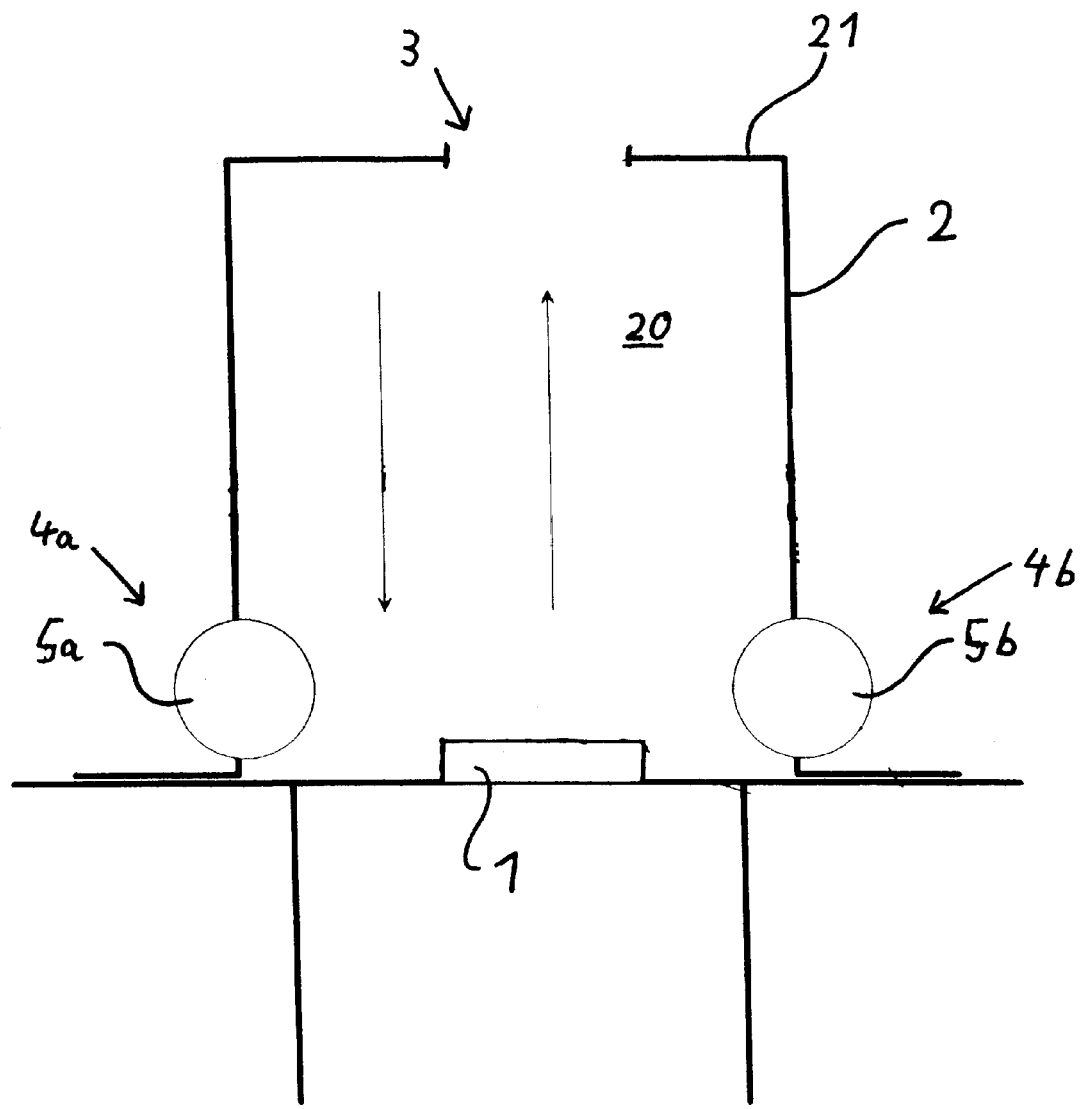
FIG. 1 is a schematic drawing of a sectional view of a first embodiment of the inventive semiconductor gas sensor.

According to FIG. 1, the semiconductor gas sensor includes in a preferred embodiment of the invention, a sensor element 1 housed in a housing 2. On the upper side 21 of the housing 2 there is an opening 3 which connects the interior 20 of the housing 2 to areas located outside the housing or to the exterior. In the bottom part of the housing 2 there are additional openings 4a, 4b. During the measurement operation, the sensor element 1 is heated whereby the air or the gas in the areas above heats up and rises. The gas flows through the additional openings 4a, 4b from the outside into the interior 20, and escapes through the opening 3 on the upper side. The gas stream is driven by means of convection through the interior of the sensor.

In the embodiment of FIG. 1, the additional openings 4a, 4b are affixed in the side walls of the housing 2 in its bottom part. The result of the convection of the heated air or the heated gas is a chimney effect, which guides the gas stream to the sensor element 1. Thus, this chimney effect no longer counteracts the gas diffusion, but rather interacts with it. The use of the chimney effect increases the response speed. Thus, a pump effect is produced, by means of which the gas to be measured is drawn into the housing 2 owing to the chimney effect. Owing to this pump effect, the gas reaches the sensor element 1 unimpeded. Reaction products, produced due to the sensor mechanism, are carried away through the utilization of convection or the chimney effect and the special arrangement of the openings 3, 4a, 4b. Thus, the time response is significantly improved.

A prior art sensor element, as described in detail, for example, in the aforementioned article by B. Ruhland et al. can be used as the sensor element 1. It comprises a gas sensitive layer, whose electric conductivity or ohmic resistance changes as a function of the respective gas concentration. To this end, metal oxide layers, made in particular of $SnO_2$, are suitable. The sensitive layer of the sensor element 1 has means to measure the electric conductivity or the electric resistance, for example in the form of a pair of contact electrodes. A heating element in the form of a platinum heating resistor is coupled by way of a $SiO_2$ layer or passivation layer to the sensitive layer. Below this layer is a substrate membrane made of $Si_3N_4$ in order to support the arrangement. The arrangement is mounted on a wafer, in the present case on a silicon substrate.

With respect to the rest of the construction of the prior art sensor element 1 and its functionality, explicit reference is made to the aforementioned article. However, it is also possible to use other prior art sensor elements, such as thick layer sensor, which deliver a measurement signal as a function of the respective gas, with which they make contact.

In the embodiment shown here, the housing 2 is made of metal. However, other materials, for example silicon, are also possible.

The upper part of the housing 2 can also be designed as a removable cover. The temperature of the sensor element 1 is set as a function of the application purpose or the gas to be measured. For example, there is a significant $NO_2$ sensitivity at relatively low temperatures ranging from approximately 50 degrees C to approximately 200 degrees C, whereas a suitable measurement temperature for CO lies, for example, in the range of 300 degrees C to 400 degrees C. Owing to the varying sensitivity at different temperatures it is possible to determine different gas components by means of an array of sensor elements 1, which are disposed in the bottom part of the chamber 1. On the other hand, it is also possible, when measuring with the sensor element 1, to set step by step different temperature ranges in order to determine or analyze the different gas components.

In the preferred embodiment, the openings 4a, 4b, which form the gas inlet, exhibit perfusible element 5a, 5b. Depending on the measurement purpose, the perfusible elements 5a, 5b can serve the purpose of filtering the gas and/or chemical and/or catalytic reaction of the gas. For this purpose, they are designed as filters or provided with passages or holes. They can also be designed porous. A metal oxide coating, for example of $SnO_2$, on the inside surfaces of the perfusible elements 5a, 5b, results in a reduction of $O_3$ to $O_2$, when the gas flows into the housing 2. Thus, the relatively high $O_3$ sensitivity which occurs in thin sensitive layers of the sensor element 1, can be equalized or reduced. Other coatings, for example made of oxidizing materials, especially palladium, effect a transformation from long stable molecules into short chains, which react better with a thin sensitive layer. In this case, the measurement sensitivity is increased. Hence, depending on the measurement purpose, different perfusible elements 5a, 5b are disposed in the openings 4a, 4b. However, the openings 4a, 4b can also be free, when a filtering or reaction of the gas components upon entry into the housing 2 is not necessary.

Figure 2:
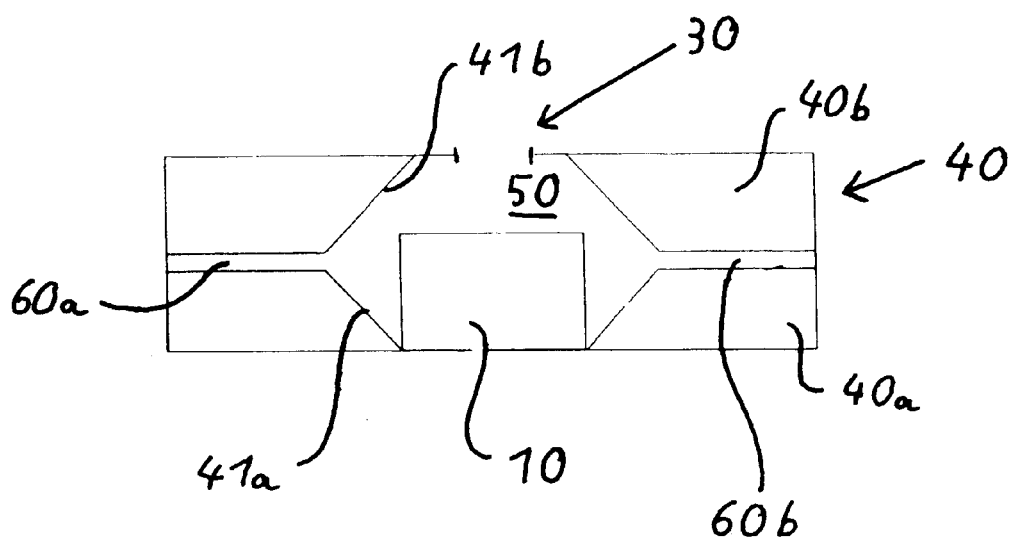
FIG. 2 is a schematic drawing of another embodiment of the inventive semiconductor gas sensor.

FIG. 2 is a schematic drawing of a cross section of another embodiment of the present invention. The sensor element 10 is integrated into a housing 40, which is made of silicon. The housing 40 consists of a bottom part 40a and an upper part 40b, both of which are designed in the shape of troughs. Both housing parts 40a, 40b are plate-shaped, whereby a notch or recess 41a, 41b is physically removed from the central area of the respective plate, in order to receive the sensor element 10. The two housing parts 40a, 40b are stacked in such a manner that the recesses 41a, 41b lie opposite each other and thus form the interior 50 of the housing 40. The upper side of the housing 40 has an opening 30, which forms the gas outlet. Between the housing parts 40a, 40b there are passages 60a, 60b in the form of channels. These passages or other openings 60a, 60b form the gas inlet on the sides of the housing 40. The recesses or troughs 41a, 41b and the channels 60a, 60b can be produced by means of customary etching techniques, known in silicon micro engineering. The result is an especially economical production for a compact type of construction, which is suitable for mass production.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A semiconductor gas sensor, comprising:
   a heatable sensor element for measuring gas concentrations and a housing, having an interior in which the sensor element is disposed,
   whereby the housing is made of silicon by means of micro-engineering and includes a first opening, which connects an interior to the exterior,
   wherein the housing has at least one second opening, which lies below the first opening, whereby the first opening is arranged above the heatable sensor element, in order to produce a chimney effect by heating the sensor element during operation.

2. The semiconductor gas sensor, as claimed in claim 1, wherein at least one second opening is arranged on the side walls in the bottom part of the housing; and the first opening is arranged on an upper side of the housing.

3. The semiconductor gas sensor, as claimed in claim 2, wherein the at least one second opening is arranged on the same level or lower than the sensor element.

4. The semiconductor gas sensor, as claimed in claim 2, wherein the sensor element is integrated into two silicon troughs, which are stacked one above the other, whereby the at least one second opening is formed between their mutual interfaces.

5. The semiconductor gas sensor, as claimed in claim 1, wherein the at least one second opening is arranged on the same level or lower than the second element.

6. The semiconductor gas sensor, as claimed in claim 5, wherein the sensor element is integrated into two silicon troughs, which are stacked one above the other, whereby the at least one second opening is formed between their mutual interfaces.

7. The semiconductor gas sensor, as claimed in claim 5, wherein a perfusible element for filtering and/or reaction of the gas is disposed in the second opening, which enables the gas to enter.

8. The semiconductor gas sensor, as claimed in claim 1, wherein the sensor element is integrated into two silicon troughs, which are stacked one above the other, whereby the at least one second opening is formed between their mutual interfaces.

9. The semiconductor gas sensor, as claimed in claim 8, wherein the first opening is formed in the top silicon trough over the sensor element.

10. The semiconductor gas sensor, as claimed in claim 9, wherein the at least one second opening is formed by means of channels, located between the silicon troughs.

11. The semiconductor gas sensor, as claimed in claim 8, wherein the at least one second opening is formed by means of channels, located between the silicon troughs.

12. A semiconductor gas sensor, comprising:
a heatable sensor element for measuring gas concentrations and a housing, having an interior in which the sensor element is disposed,
whereby the housing is made of silicon by means of micro-engineering and includes a first opening, which connects an interior to the exterior,
wherein the housing has at least one second opening, which lies below the first opening, whereby the first opening is arranged above the heatable sensor element, in order to produce a chimney effect by heating the sensor element during operation wherein a perfusible element for at least one of filtering and reaction of the gas is disposed in each of the at least one second opening, which enables the gas to enter.

13. The semiconductor gas sensor, as claimed in claim 12, wherein the inside surfaces of the perfusible element exhibit a material that subjects the gas flowing through to a chemical and/or catalytic reaction, before said gas reaches the sensor element.

14. A process for measuring gas concentrations with a semiconductor gas sensor, comprising the steps of:
providing a heatable sensor element arranged in a housing made of silicon by means of micro-engineering;
heating a gas located over the sensor element; and
driving a gas stream in the form of a chimney whereby the gas flows through the housing by means of first and second openings so that the gas flows from the bottom of the housing to the top of the housing and is guided past the sensor element in order to produce a measurement signal as a function of the gas concentration.

15. The process as claimed in claim 14, wherein said gas is one of filtered and reacted, before said gas makes contact with the sensor element.

16. A process for measuring gas concentrations with a semiconductor gas sensor, comprising the steps of:
providing a heatable sensor element arranged in a housing made of silicon by means of micro-engineering;
heating a gas located over the sensor element; and
driving a gas stream in the form of a chimney whereby the gas flows through the housing by means of first and second openings so that the gas flows from the bottom of the housing to the top of the housing and is guided past the sensor element in order to produce a measurement signal as a function of the gas concentration wherein a perfusible element for at least one of filtering and reaction of the gas is disposed in the second opening, which enables the gas to enter.

* * * * *